United States Patent [19]

Olsen

[11] 3,976,383
[45] Aug. 24, 1976

[54] VISUAL METHOD OF LOCATING FAULTS IN PRINTED CIRCUIT BOARDS
[75] Inventor: Oliver Albert Olsen, Old Bridge, N.J.
[73] Assignee: The Bendix Corporation, Teterboro, N.J.
[22] Filed: Feb. 28, 1975
[21] Appl. No.: 553,943

[52] U.S. Cl.............................. 356/166; 356/168; 356/237
[51] Int. Cl.² ..................... G01B 9/08; G01N 21/16
[58] Field of Search ........... 356/164, 165, 166, 168, 356/237

[56] References Cited
UNITED STATES PATENTS
3,711,205  1/1973  Tulk et al. ......................... 356/237
3,713,741  1/1973  Sheehan ............................. 356/165

Primary Examiner—Vincent P. McGraw
Attorney, Agent, or Firm—Anthony F. Cuoco; S. H. Hartz

[57] ABSTRACT

A method of visually detecting defects in a printed circuit board comprising preparing a mask with a light blocking pattern corresponding to the desired printed circuit, illuminating the printed circuit board through the mask with the light of a color complimentary to the color of the printed circuit board and with the light blocking pattern in registry with the printed circuit and inspecting the printed circuit board for light reflected from defects in the printed circuit not present in the light blocking pattern on the mask. The defects are readily apparent as bright spots on a dark background.

7 Claims, 4 Drawing Figures

VISUAL METHOD OF LOCATING FAULTS IN PRINTED CIRCUIT BOARDS

FIELD OF THE INVENTION

The invention relates to detecting defects visually in printed circuit boards.

PRIOR ART

A circuit board passed through a flow solder machine may pick up excess solder between two circuit elements and cause a short circuit. These defects are difficult to locate because they often look authentic to an inspector. If these defects are not located before the printed circuit board is energized, the printed circuit board and/or the circuit components may be damaged or destroyed. This is costly even when the defects can be corrected and the circuit components replaced. In some instances a circuit component is not destroyed, but its life is seriously impaired. This cannot be tolerated, especially in aerospace industries where lives are at stake and even in other industries where warranties are in effect.

Heretofore defects in printed circuit boards were detected either by direct comparison or by electrical tests. Direct comparison is extremely tedious and ineffective. Equipment for testing printed circuit boards is expensive, difficult to program and inflexible. Also, the equipment, especially contact mechanisms, requires a great deal of maintenance. Self-programming equipment involves computers and sophistocated hardware and is even more expensive.

One device for comparing two circuit boards uses a blink machine which alternatively illuminates the printed circuit boards being compared at a rate which can be programmed. This method is not satisfactory because although the printed circuit pattern may be the same, there may be many details in the circuit boards that differ and this confuses the operator. The method is so tedious on crowded printed circuit boards that the inspectors are fatigued to the point of uselessness after a few boards are inspected.

SUMMARY OF THE INVENTION

The present invention relates to an optical method of locating faults, such as bridging or solder shorts, in printed circuits on a printed circuit board or other substrate. The method is based on two optical principles, (1) that metals used to conduct electricity are highly reflective and (2) a colored material illuminated by the light of a complimentary color will emit little or no light. To detect unwanted conductors on the printed circuit board or substrate, only the area in which no conductors are supposed to exist is illuminated with light of a color complimentary to the color of the substrate or printed circuit board. For example, a green printed circuit board is illuminated with a red light and the light is prevented from illuminating the wanted printed circuit. If unwanted conductors are present on the board or substrate they will be illuminated and reflect light so that they will be readily visible and easily located on a dark background because of the absorption of light by the board or substrate.

The method may be implemented in several ways. A direct overlay having a black printed circuit pattern may be used to mask the conductors in the printed circuit. The overlay may include a suitable filter for providing light of a color complimentary to the color of the board or substrate so that the board or substrate absorbs the light passing through the filter. When the circuit board is illuminated through the overlay, if there is a defect in the circuit, that is, a conductor in an illuminated area, it will show up as a bright spot the same color as the filter. Defects in the printed circuit are readily detectable since the defects appear as bright spots on a dark background. This method does not require any expensive equipment and most defects are detected with relative ease.

In some instances it may be desirable to project the circuit board pattern from a film onto the circuit board with the circuit pattern image in registry with the printed circuit using light of a color complimentary to the color of the circuit board as described above either by using the proper light source or by filtering. Any unwanted conductors on the circuit board show up as bright spots, the same color as the light source or filter on a dark background. Small defects are visible and the defects can be marked directly without first removing an overlay as described above. This arrangement is especially desirable where the circuit board has projections or uneven surfaces which would interfere with the overlay.

The invention comtemplates a method of visually detecting defects in a printed circuit on a printed circuit board, comprising preparing a mask with a light blocking pattern corresponding to the desired printed circuit illuminating the printed circuit board through the mask with a light of a color complimentary to the color of the printed circuit board, and with the light blocking pattern in registry with the printed circuit, and inspecting the printed circuit board for light reflected from defects in the printed circuit not present in the light blocking pattern on the mask.

THE DRAWING

FIG. 1 shows an overlay having a light blocking pattern corresponding to the printed circuit, FIG. 2 shows a corresponding printed circuit on a circuit board having a defect, FIG. 3 shows the overlay of FIG. 1 in registry with the circuit board of FIG. 2 in which the defect in the printed circuit shows as a bright spot on a dark background in accordance with the invention, and FIG. 4 shows a second embodiment of the invention in which an image of the light blocking pattern is projected in registry with the printed circuit on the printed circuit board.

DETAILED DESCRIPTION OF THE INVENTION

Figure 1:
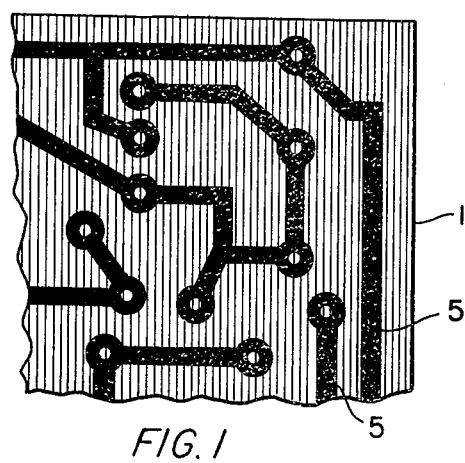
Figure 2:
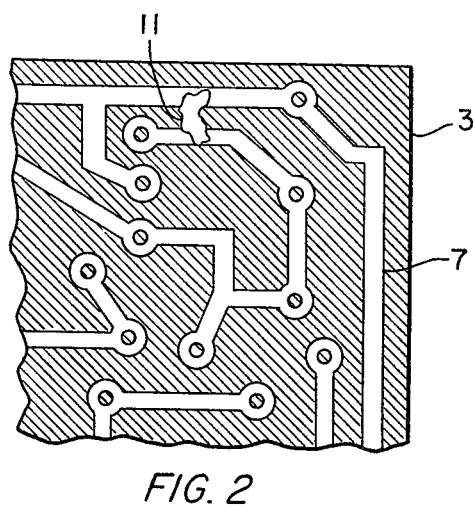
Figure 3:
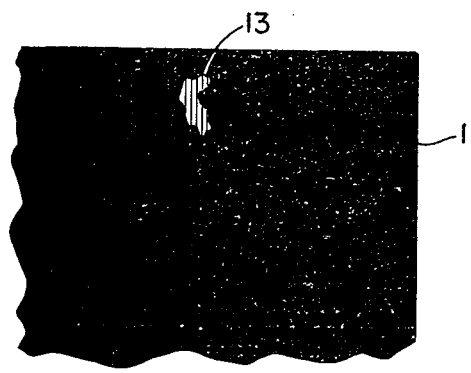

Referring to the drawing, to implement the invention to mask 1 of the kind shown in FIG. 1 may be made from the art work used in making a printed circuit board 3 as shown in FIG. 2. In the mask the black line pattern 5 corresponds to the conductors in the printed circuit 7. In the arrangement shown in the drawing the circuit pattern 5 on mask 1 is made with a 1-1 relationship with printed circuit 7 on printed circuit board 3. The remainder of the mask may be transparent or translucent and of a color complimentary to the color of the printed circuit board or substrate. The mask is overlayed on the printed circuit board as shown in FIG. 3 with the circuit pattern in registry with the printed circuit. A light source 9, such as white light, is used to illuminate the mask which filters the light and passes only the color complimentary to the circuit board or substrate in areas where there is no wanted printed circuit. The black line circuit pattern on the mask prevents illumination of the desired printed circuit. Only the circuit or substrate and unwanted conductors are illuminated. If the circuit board has a defect, such as excess solder 11 not present in the circuit pattern on the mask, this will appear to the inspector as a bright spot 13 on a dark background. The reason for this is that no light of a complimentary color is reflected from the circuit board, but light illuminating a circuit conductor or solder will be reflected as a bright spot having the color of the complimentary color used.

Figure 4:
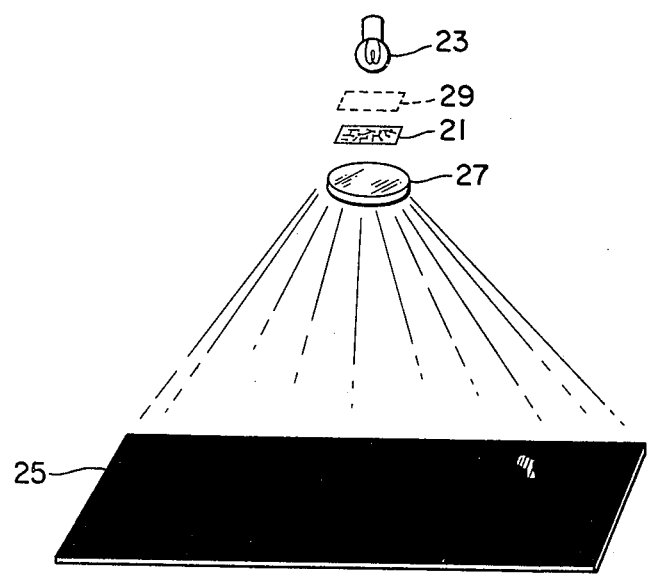

Instead of making the mask with a circuit pattern in a 1-1 relationship with the printed circuit, as described above, a small film 21, such as a microfilm aperture card, can be used instead. The printed circuit pattern on the film is projected by a light source 23 of a color complimentary to the color of the printed circuit board 25 and imaged by a lens 27 on the printed circuit board in registry with the printed circuit so that no light is projected on the wanted printed circuit as shown in FIG. 4. If any unwanted conductor exists it will show up as a bright spot the same color as the complimentary color on a dark background.

The complimentary color may be provided by using either a colored source or a white light source and suitable filter 29 shown in dotted lines. This arrangement has the advantage that small defects are visible and a defect can be marked directly without removing a mask as in FIG. 3. Also, if the circuit board has projections or is otherwise uneven, it will present no problem as it may when using a mask.

The present invention provides a method of visually detecting defects in a printed circuit on a printed circuit board before they are assembled in an electrical circuit and avoids damage that may occur if the circuit boards are energized with a short circuit connection. The method is much faster than direct inspection and relatively inexpensive in comparison to sophistocated electrical methods. If changes are made in the printed circuit the art work for the new printed circuit board may be used to make a new mask for inspection purposes.

What is claimed is:
1. A method of visually detecting defects in a printed circuit on a printed circuit board, comprising preparing a mask with a light blocking pattern corresponding to the desired printed circuit, illuminating the printed circuit board through the mask with a light of a color complimentary to the color of the printed circuit board and with the light blocking pattern in registry with the printed circuit, and inspecting the printed circuit board for light reflected from defects in the printed circuit not present in the light blocking pattern on the mask.

2. A method of visually detecting defects in a printed circuit on a printed circuit board as described in claim 1 in which the light blocking pattern on the mask has the same dimensions as the printed circuit and the mask is overlayed on the printed circuit board with the pattern in registry with the printed circuit.

3. A method of visually detecting defects in a printed circuit on a printed circuit board as described in claim 1 in which the light blocking pattern on the mask is projected by a projector and imaged on the printed circuit board in registry with the printed circuit.

4. A method of visually detecting defects in a printed circuit on a printed circuit board as described in claim 3 in which the circuit pattern on the mask is substantially smaller than the printed circuit and the projected pattern is enlarged to the size of the printed circuit.

5. A method of visually detecting defects in a printed circuit on a printed circuit board as described in claim 1 in which the mask is illuminated by white light and the mask filters the white light to provide the complimentary color.

6. The method of visually detecting defects in a printed circuit on a printed circuit board as described in claim 1 in which a source of white light is used and a separate filter filters the white light to provide the complimentary color.

7. A method of visually detecting defects in a printed circuit on a printed circuit board as described in claim 1 in which a source of light having a complimentary color is used.

* * * * *